United States Patent
Reynolds et al.

[11] Patent Number: 5,921,676
[45] Date of Patent: Jul. 13, 1999

[54] UNDULATING MIXING DEVICE WITH ADJUSTABLE TILT AND METHOD

[75] Inventors: Cedric S. Reynolds; Terrence J. Gilbert, both of Greensboro, N.C.

[73] Assignee: Stovall Life Science, Inc., Greensboro, N.C.

[21] Appl. No.: 09/013,009

[22] Filed: Jan. 26, 1998

[51] Int. Cl.$^6$ .................................................. B01F 11/00
[52] U.S. Cl. ............................................................ 366/208
[58] Field of Search ........................... 366/110–112, 114, 366/208–217, 219

[56] References Cited

U.S. PATENT DOCUMENTS

| | | | |
|---|---|---|---|
| 2,192,233 | 3/1940 | Mack | 366/111 |
| 2,552,188 | 5/1951 | Krause et al. | 366/215 |
| 2,834,585 | 5/1958 | O'Harenko . | |
| 3,607,478 | 9/1971 | Henninges et al. | 366/208 |
| 3,788,611 | 1/1974 | Barbini . | |
| 3,985,307 | 10/1976 | Ebbert et al. . | |
| 4,061,315 | 12/1977 | Eitzen et al. | 366/111 |
| 4,118,801 | 10/1978 | Kraft et al. | 366/111 |
| 4,125,335 | 11/1978 | Blume et al. | 366/209 |
| 4,305,668 | 12/1981 | Bilbrey | 366/111 |
| 4,702,610 | 10/1987 | Reynolds, Jr. | 366/213 |
| 4,893,938 | 1/1990 | Anderson | 366/208 |
| 5,423,603 | 6/1995 | Reynolds et al. | 366/208 |
| 5,639,160 | 6/1997 | Kishimoto | 366/208 |

FOREIGN PATENT DOCUMENTS

91/10503  7/1991  WIPO ................................. 366/209

OTHER PUBLICATIONS

Elmeco brochure, date unknown.

*Primary Examiner*—Charles E. Cooley

[57] ABSTRACT

An undulating mixing device comprises a base and a platform connected by four flexible connectors which includes a base and a platform connected by four flexible connectors. The base includes a planar portion supporting an x-shaped housing. In the corners created by the x, the flexible connectors are attached to the planar portion of the base. A tilt assembly including a collar adjustably joins the base to the platform and controls the tilt or yaw movement of the platform as a motor moves the platform in a circular motion.

16 Claims, 10 Drawing Sheets

5,921,676

UNDULATING MIXING DEVICE WITH ADJUSTABLE TILT AND METHOD

BACKGROUND OF THE INVENTION

1. Field of the Invention

This invention pertains to an undulating mixing device for agitation of solutions in a laboratory environment.

2. Description of the Prior Art and Objectives of the Invention

Lab technicians frequently have to agitate, stir or blend solutions which are very delicate, such as during protein, DNA and RNA staining operations where vigorous agitation may ruin the samples.

In recent years, several devices have been promoted which gently agitate solutions in laboratory environments, such as U.S. Pat. Nos. 4,702,610; 4,893,938; and 5,423,603. Such devices are desirable in general to automate a tedious procedure and to perform agitation in a smooth fashion without the introduction of bubbles or froth. Likewise, gentle vertical agitation mixes solutions which have components with different specific gravities, thereby preventing layers from forming which may inhibit the completion of a desired chemical reaction.

One problem not addressed by these prior devices is that they have a predetermined degree of tilt between the platform and the base which remains the same during agitation. Frequently, this degree of tilt is too pronounced or undesired for the task at hand. Or it could be too little to properly mix a solution with components having drastically different specific gravities, and again, the degree of the tilt cannot be easily changed to accommodate desired increased vertical agitation.

A second problem associated with prior mixing devices is that footprint of the device is relatively large. When the solution must be agitated under pressure or in certain controlled environments where space is a premium, such as an incubator or refrigerated unit, this large foot print may take up the majority of the interior space. If solutions must be agitated at different speeds, such space is rapidly filled by a plurality of mixing devices. The obvious solution of increasing the vertical dimension of the mixing device is not acceptable because an increase in any dimension of the mixing device is undesirable.

With the above concerns in mind, it is an objective of the present invention to provide an undulating mixing device with a tiltable platform wherein the tilt angle is selectively adjustable.

It is another objective to provide an undulating mixing device whose undulating motion combines orbital movement and selective rocking movement of the platform.

It is a further objective of the present invention to provide a mixing device with a small footprint by utilizing an x-shaped housing which contains the motor and the electrical circuitry.

It is still a further objective of the present invention to provide a mixing device with a relatively small vertical dimension.

It is yet a further objective of the present invention to provide a mixing device with a rotatable collar for adjusting the tilt of the platform by lengthening or shortening the distance between the platform and the base.

It is another objective to provide a method of using the mixing device described herein.

These and other objectives and advantages will become readily apparent upon further reference to the following detailed description and drawings.

SUMMARY OF THE INVENTION

The aforesaid and other objectives are realized by providing a mixing device with a base including a planar portion and a housing, wherein the housing is preferably metal and x-shaped. An electric cord supplies conventional alternating current energy to the device and the electronics contained within the housing. A knob connected to the electronics within the housing provides manually adjustable speed control for the motor. The motor is indirectly joined to an arm in the center of the base. Four flexible connectors, preferably polyvinyl chloride tubing connect the planar portion of the base to a planar platform. The platform is spaced above the housing and is indirectly attached to the arm in such a manner as to make the center of the platform offset from the center of the base by essentially the length of the arm. As the arm rotates horizontally due to the rotation of the motor, the platform is thereby moved in a restricted circular or orbital manner. The flexible connectors are attached to the base in the recesses of the x-shaped housing and to the platform corners. The flexible connectors induce a tilt into the platform as it orbits over the base. When the corner of the platform is directly over the recess of the x-shaped housing so that the flexible connector is substantially non-distorted, that corner is at its highest point, while the opposite corner is at its lowest point. In turn each corner is raised and lowered as the platform orbits.

The arm is rigidly connected to the motor shaft, and the arm is also connected to a pivot shaft by conventional press pins. The pivot shaft is pressure fit into a 0.375 inch (0.953 cm) bore ball bearing to accommodate the orbiting motion. The collar is positioned on top of the ball bearing and rotates relative to the pivot shaft. The pivot shaft allows the collar to tilt freely away from a vertical orientation as needed. The interior of the collar is threaded and receives a threaded post. The threaded post is biased by a tensioned spring that rests on an interior floor on the collar and abuts the interior surface of the threaded post. In normal operation, the arm rotates as the motor turns the motor shaft. Thus the distal end of the arm circumscribes an orbital path around the motor shaft, which is located in the center of the base. The collar rotates relative to the arm's motion, but in general is dragged through this orbital path by the arm's motion. The threaded post is rigidly affixed to the platform, and, as the collar moves in the orbital path, the threaded post and the platform circumscribe a like path. The threaded post is affixed to the center of the platform, thus, the platform and the base are centrally offset. This offset causes the platform to define a restricted, eccentric orbit over the base.

When the threaded post is raised by selectively, manually, turning the collar, it effectively raises the platform from the base, and the flexible connectors are thus stretched or extended upwardly so as to keep equal tension on all four corners of the platform. When the platform is rotated while in this elevated position, little or no tilting occurs. However, when the platform is lowered by turning the collar, the flexible connectors are compressed and are forced downwardly in sequence at the corners of the platform. The pivot post allows the collar to assume a non-vertical position and this correspondingly allows the platform to tilt. When the platform is rotated in this lowered position, tilt is induced into the platform by the distorted flexible connectors. As the platform swings in eccentric orbital fashion, each flexible connector in turn becomes straight with its corresponding corner of the platform at its highest point above the base. The remaining flexible connectors are compressed to some degree and their corresponding corners are at varying heights above the base. Each flexible connector in turn induces a tilt to the platform as the platform rotates. Thus, by selectively, manually raising or lowering the threaded post within the collar, and hence raising or lowering the platform above the base, a different amount of tilt is provided.

Sometimes a lab technician wants only a horizontal or swirling agitation in the solution. At other times, a combination of horizontal and vertical agitation is desired, and this can be accomplished with the same mixer whereas prior art mixers allowed either pure horizontal mixing or horizontal and only a predetermined amount of vertical mixing. The present invention allows the lab technician to select the exact degree of vertical agitation introduced in the solution by the orbital motion of the mixer. This provides better mixing at slow speeds and better coverage since the liquid has two currents introduced, namely a horizontal current and a vertical cross current. Herein, orbital is taken to mean any circular motion, whether it be purely horizontal or whether it be at an angle relative to a fixed plane.

DETAILED DESCRIPTION OF THE PREFERRED EMBODIMENT AND OPERATION OF THE INVENTION

Figure 1:
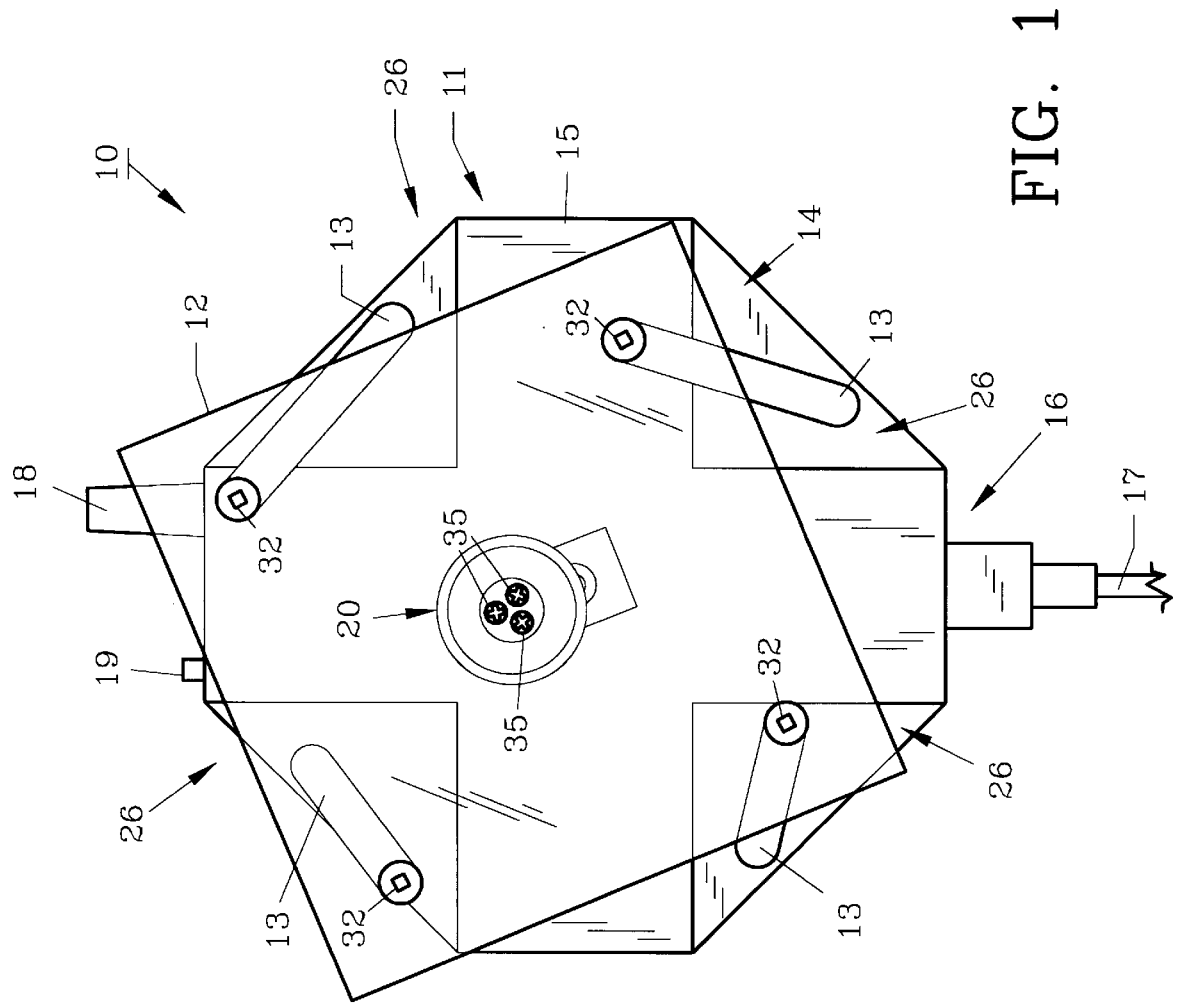
FIG. 1 shows a top down view of the preferred mixing device of the present invention.

Turning now to the drawings, specifically FIG. 1 shows a top view of preferred mixing device 10. Mixing device 10 includes base 11 and platform 12. Platform 12 is preferably a rigid transparent polymeric material cut into a generally rectangular, planar shape. Platform 12 is spaced from base 11 by flexible connectors 13 and tilt/rotation assembly 20. Base 11 is preferably metal and includes planar portion 14 and x-shaped housing 15. X-shaped housing forms corners 26 which provide space for flexible connectors 13 to be attached to planar portion 14 without increasing the size of the footprint of mixing device 10. While an x-shape is preferred, any similar shape could be used such a Y or V shape, so long as corners are formed which can receive flexible connectors 13.

As seen in FIG. 1, platform 12 is attached to flexible connectors 13 by fasteners 32 which are preferably conventional Allen head bolts. Flexible connectors 13 are preferably transparent, flexible polyvinyl chloride tubing, although other flexible connectors could be used, either polymeric, natural or metal spring material. Conventional slip ties 33 (FIGS. 2 and 3) constrict around flexible connectors 13 at the top and bottom to provide clamping to hold fasteners 32 in place, and to keep flexible connectors 13 attached to raised knobs 66 on planar portion 14. Platform 12 is attached to assembly 20 by additional fasteners 35.

Figure 2:
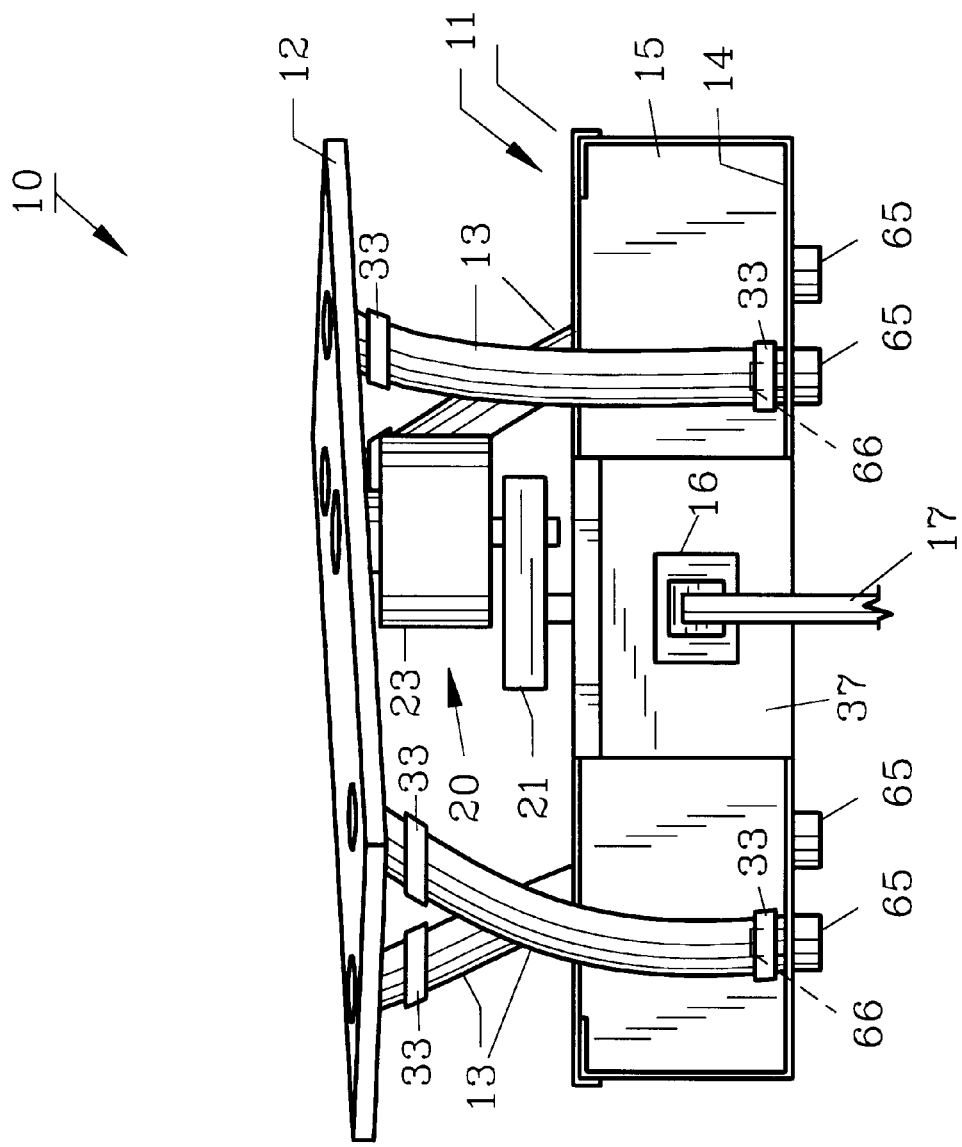
FIG. 2 illustrates a rear side view of the mixing device of FIG. 1.
Figure 3:
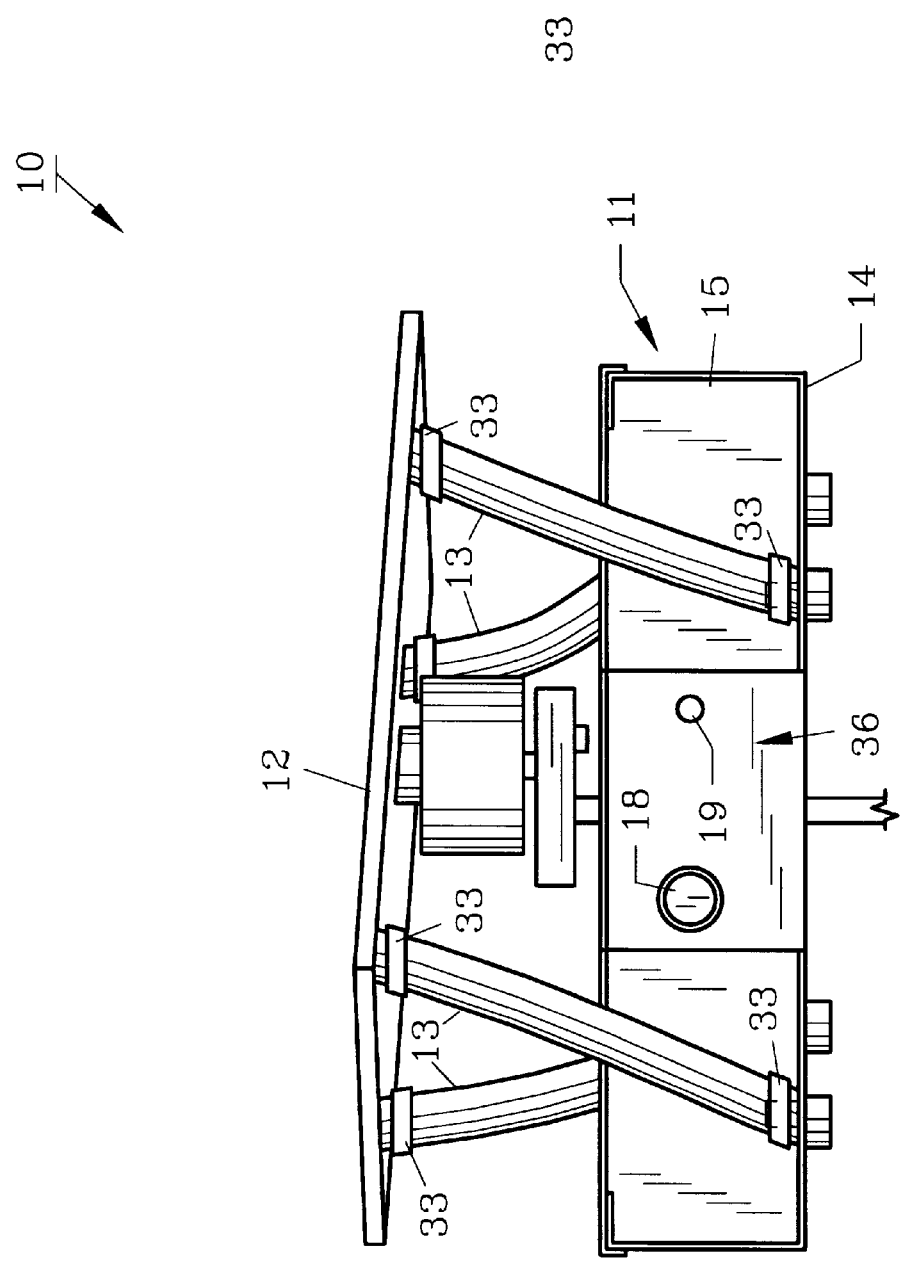
FIG. 3 demonstrates a front side view of the mixing device of FIG. 1.

Turning now to FIGS. 2 and 3 which depict side views of preferred mixing device 10, FIG. 2 illustrates conventional electric cord 17 received by conventional electrical receptacle 16, which is positioned on back side 37 of housing 15. As is well understood, cord 17 is plugged into a typical 115 V AC wall outlet (not shown) and provides power to mixing device 10. Cord 17 is preferably a three conductor cord to provide a safe ground connection. FIG. 3 shows front side 36 of housing 15. Front side 36 includes neon light 19 which is illuminated when mixing device 10 is turned on. Also seen is on/off/speed control knob 18, which is rotatably affixed to front side 36 and controls the speed of mixing device 10. Also seen are rubber feet 65 which support base 11 and insure strong resistance to sliding. It should be understood, that this device is easily adapted to a 220 V AC wall outlet for use in European markets.

Figures 7, 8:
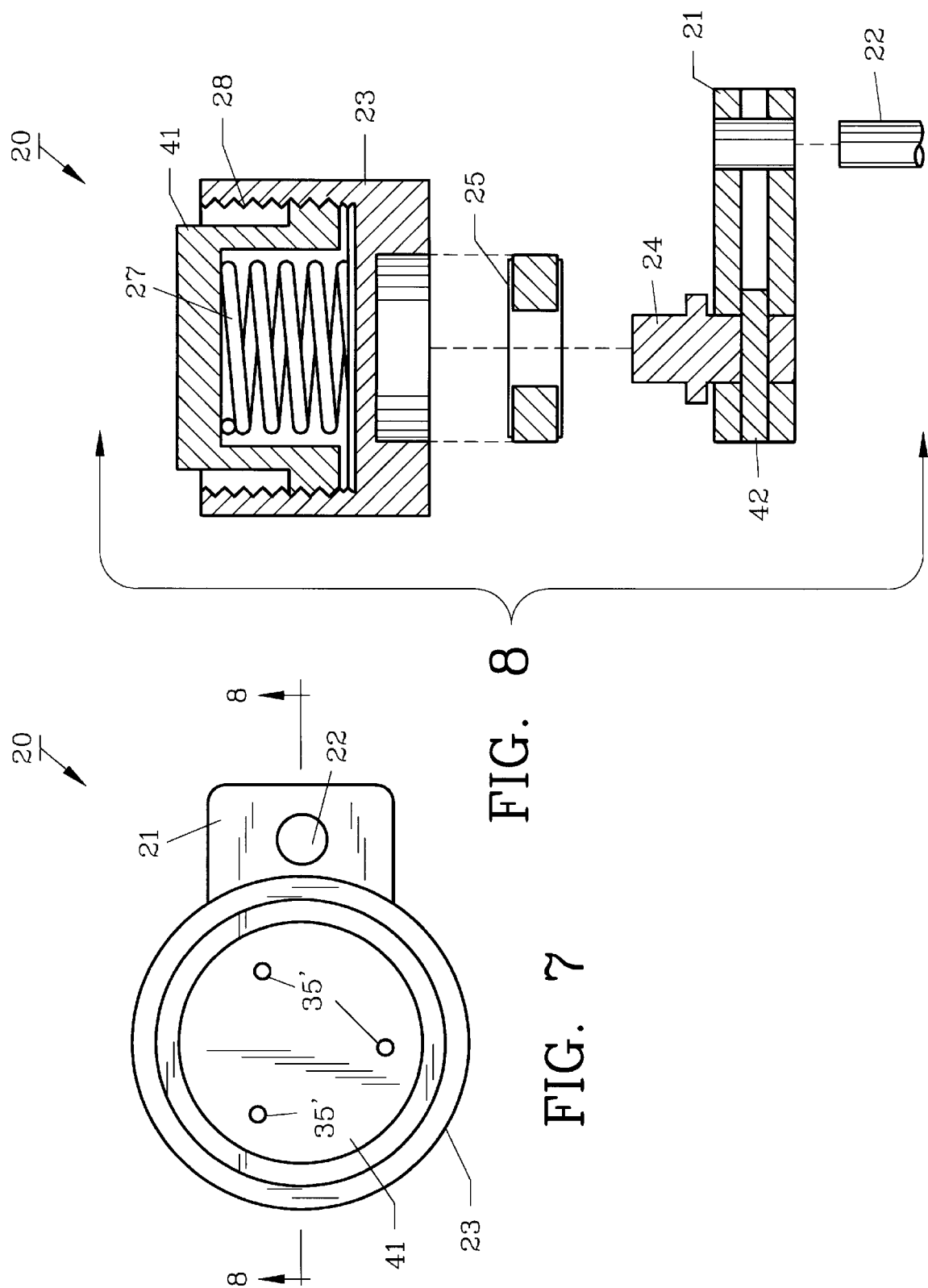
FIG. 7 shows an enlarged top view of the tilt adjusting mechanism of the mixing device.
FIG. 8 illustrates a cross sectional view of the tilt adjusting mechanism along lines 8—8 of FIG. 7.

As best seen in FIGS. 7 and 8, assembly 20 is a multi-component unit which includes arm 21, motor shaft 22, pivot shaft 24, ball bearing 25, collar 23, threaded post 41 and spring 27. Motor shaft 22 is indirectly connected to motor 51 by a pair of direction changing gears (not shown), and shaft 22 is rigidly affixed to arm 21. Arm 21 is attached to pivot shaft 24 by press pin 42 which is flushly inserted within the distal end of arm 21. Pivot shaft 24 allows collar 23 to freely tilt from its original vertical position so that platform 12 may also tilt or yaw. Motor shaft 22 is located in the center of base 11 so that the distal end of arm 21 is swung in an orbital path as motor shaft 22 is turned. Ball bearing 25 is preferably a 0.375 inch bore (0.953 cm) metal ball bearing, and pivot shaft 24 is pressure fit into bearing 25. Collar 23 is preferably metal and interiorly threaded with threads 28. Threaded post 41 is inside collar 23 and engages threads 28 and may be raised or lowered as desired. Counter-clockwise rotation of collar 23 lowers threaded post 41 and clockwise rotation of collar 23 raises threaded post 42. Spring 27 rests on the floor of collar 23 and abuts the interior surface of threaded post 41 to prevent any drift of threaded post 41 during rotation. Threaded post 41 is rigidly affixed to the center of platform 12 by fasteners 35 which are received by fastener apertures 35'.

As arm 21 orbits, collar 23 rotates via ball bearing 25 relative to arm 21 and carries threaded post 41 therewith. This movement causes platform 12 to circumscribe an eccentric orbit over base 11 since the center of platform 12 is not directly above the center of base 11. Threaded post 41 can be manually raised and lowered within collar 23, thus changing the distance between platform 12 and base 11. Since collar 23 is rotating, threaded post 41 has a tendency to "drift" downwardly on threads 28, thus changing the positioning of platform 12. Spring 27 is tensioned between collar 23 and threaded post 41 and corrects this "drifting" by biasing threaded post 41 so that threaded post 41 does not rotate downwardly within collar 23 as arm 21 moves in its circular path. As threaded post 41 is lowered within collar 23, more tension is put upon spring 27.

Figure 4:
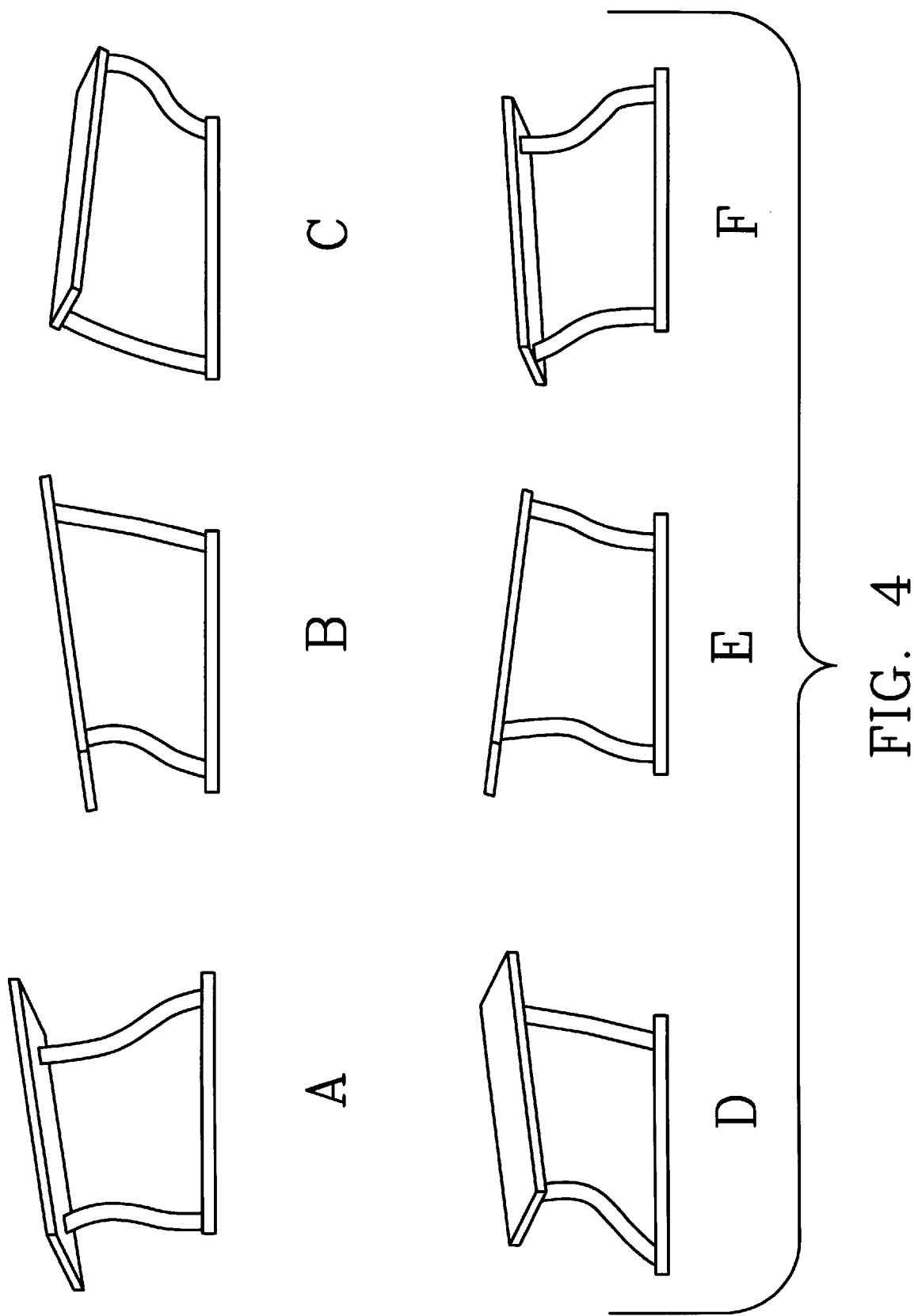
FIG. 4 features side views of the undulating platform of the present invention.
Figure 5:
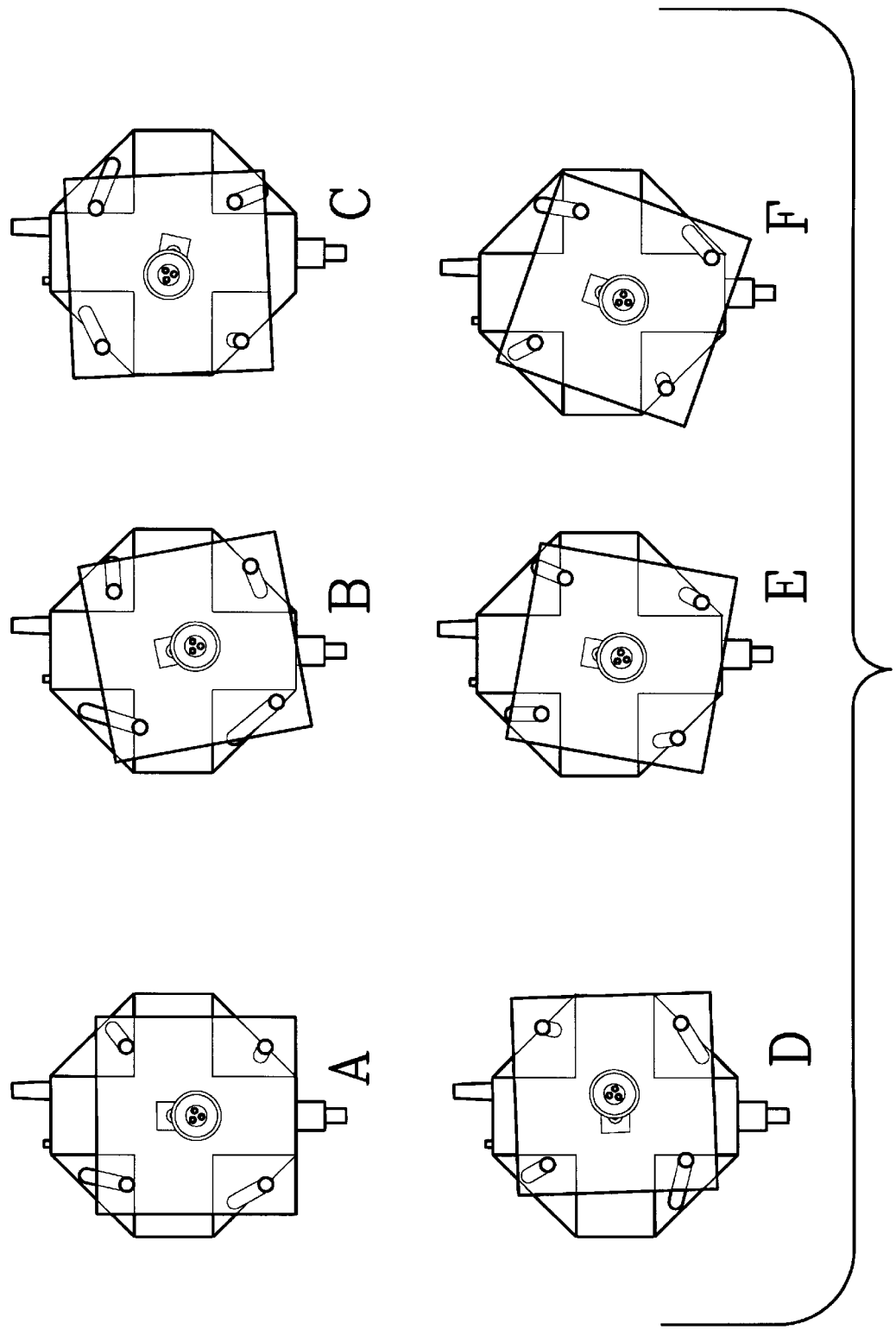
FIG. 5 pictures top views of the undulating platform of FIG. 4.

The ability to raise and lower threaded post 41 and platform 12 is impacted by the shape and positioning of tubular flexible connectors 13. When platform 12 is raised to the maximum, flexible connectors 13 are generally straight and undistorted. When arm 21 swings platform 12 in its orbit over base 11, each arm remains essentially straight and platform 12 remains level. Thus, a solution can be mixed via a horizontal swirling motion with little or no vertical agitation. However, when platform 12 is lowered, flexible connectors 13 are distorted and compressed into non-linear shapes. As platform 12 is rotated, each flexible connector 13 in turn is straightened. The corresponding corner of platform 12 is raised to its highest point above base 11 when its flexible connector 13 is straight. The remaining corners of platform 12 are in varying degrees of positions closer to base 11, with the opposite corner generally being the lowest. The flexible connectors 13 associated with these lowered corners are distorted into non-linear shapes, the amount of distortion being generally inversely proportional to the height of the corresponding corner above base 11. The lower platform 12 is, the greater the tilt. Thus, manual rotation of collar 23 raises and lowers platform 12 to allow selection of the amount or degree of tilt in platform 12 desired. The tilting of platform 12 along with the orbital path that platform 12 circumscribes causes both horizontal and vertical agitation in solutions placed on platform 12. This allows the choice of the vertical agitation induced in the solution as mixing device 10 is used. This tilting movement is illustrated and will be better understood upon examination of FIGS. 4 and 5, which sequentially provide schematic top and side views of this movement.

Figure 9:
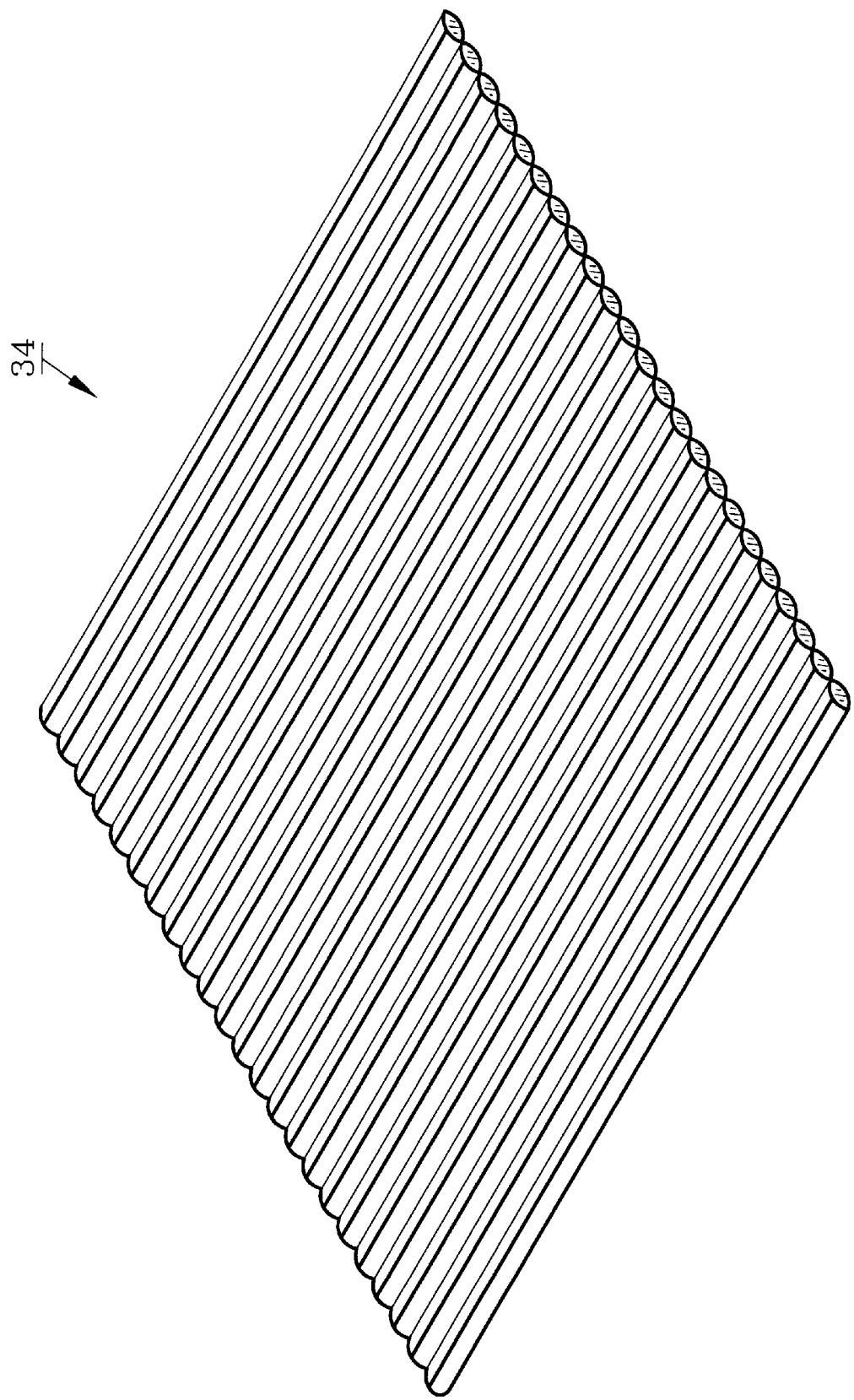
FIG. 9 demonstrates a no-slip pad which may be used on the mixing device of FIG. 1.

FIG. 9 shows commercially available rubberized no-slip pad 34 which can be placed on top of platform 12 so as to prevent items such as beakers or other containers (not shown) from sliding along tilted platform 12. No-slip pad 34 is preferably a resilient polymeric material having an irregular surface to provide additional frictional engagement.

Figure 6:
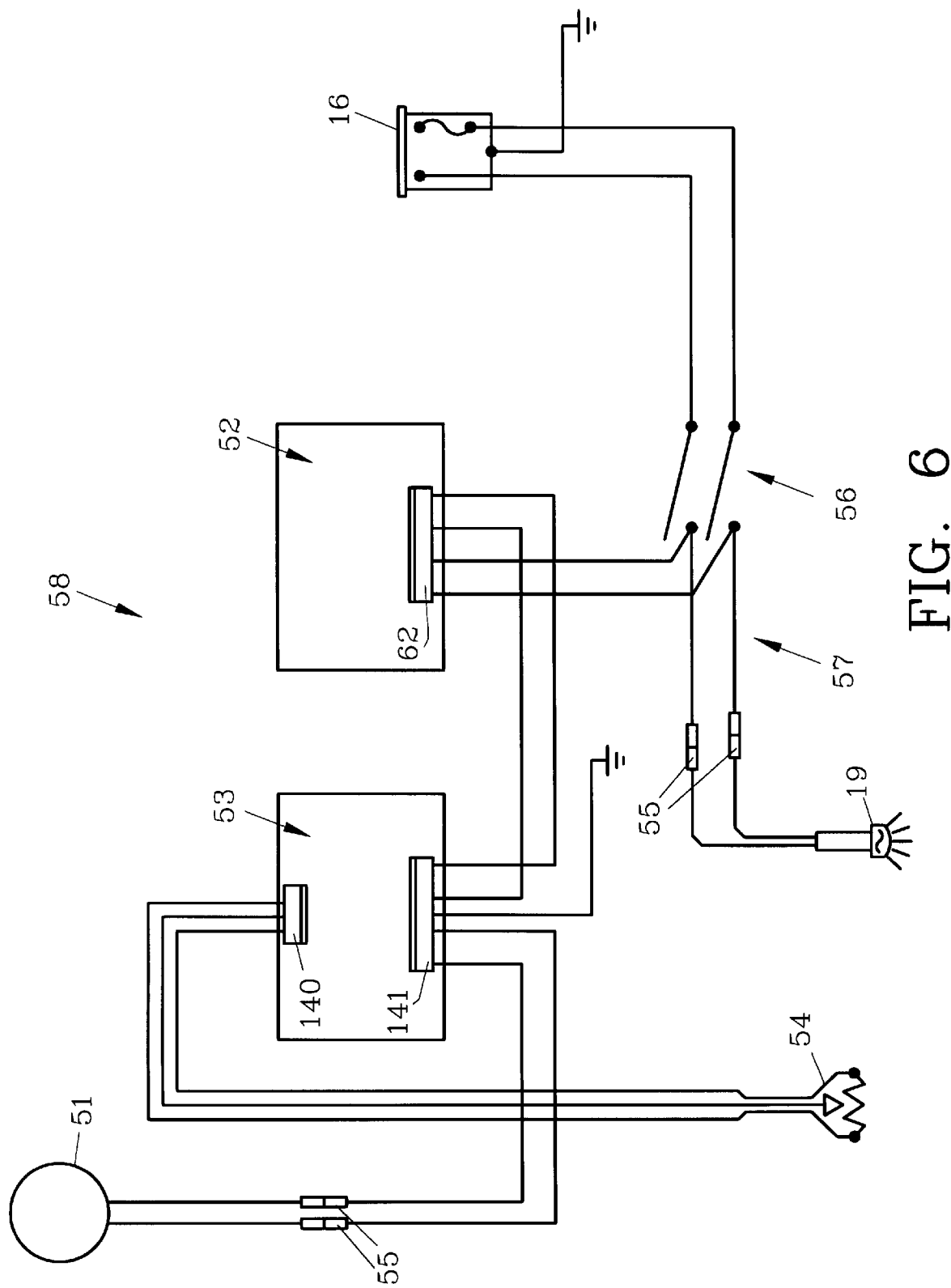
FIG. 6 depicts an electrical schematic of the mixing device of FIG. 1.

General electrical circuit 50 of mixing device 10 is seen in FIG. 6. Specifically, electrical receptacle 16 comprises a conventional IEC power entry module and is in electrical communication with power switch 56. Switch 56 completes two parallel circuits when turned on. The first part, indicated generally at 57, provides power to neon lamp 19 through a pair of molex couplings 55. The second part, indicated generally at 58, comprises voltage selector and transformer printed circuit card 52, which is in series with speed control card 53. Speed control card 53 is in electrical communication with conventional electric motor 51 and speed potentiometer switch 54. Additional molex couplings 55 are used to connect the various elements. In reality power switch 56 and speed potentiometer switch 54 are both incorporated into knob 18, as is well understood in the art. Transformer card 52 converts 115 AC volts or 230 AC volts to 24 AC volts, while motor 51 is a conventional 24 V DC electric motor.

Figure 10:
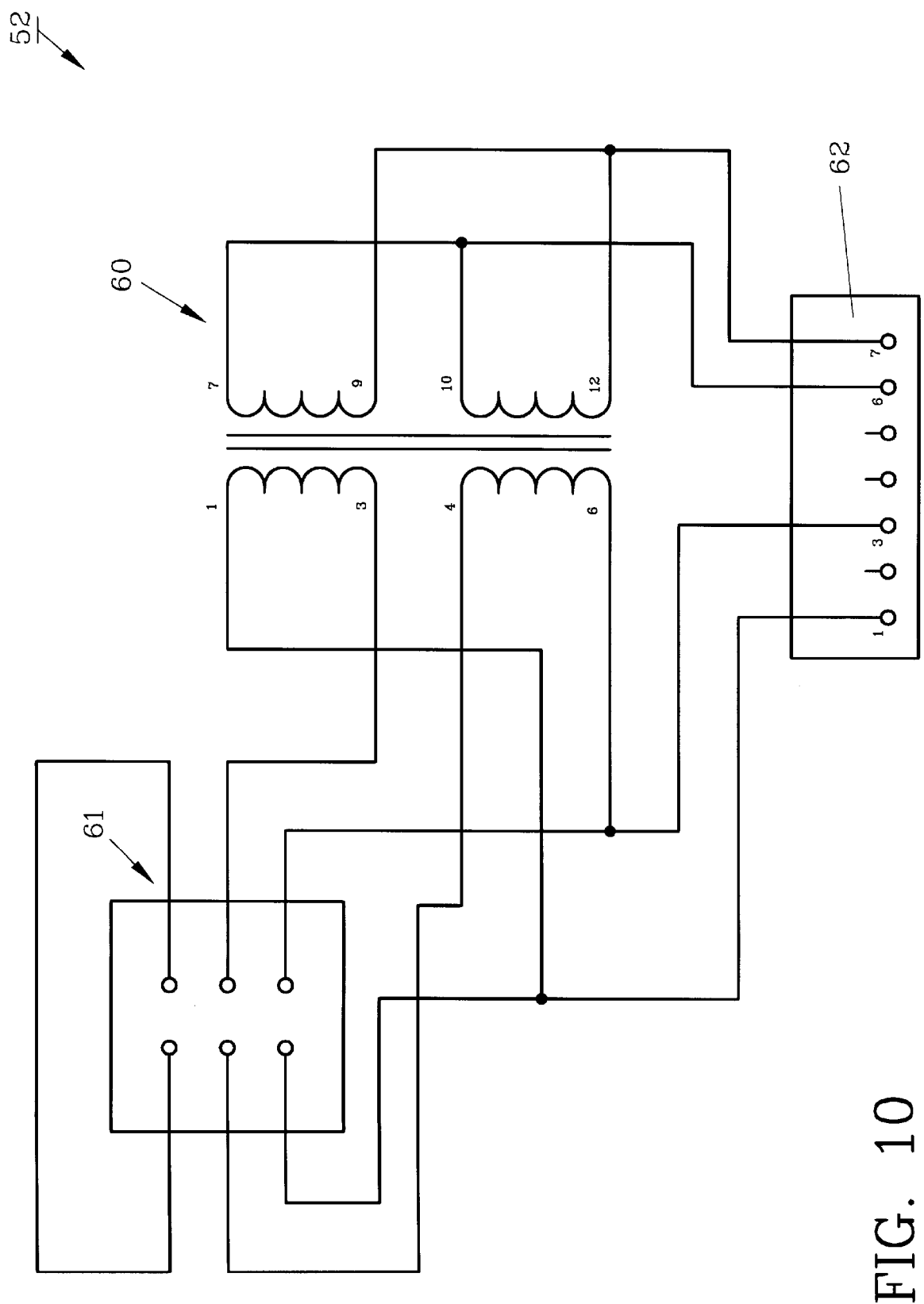
FIG. 10 shows the electrical schematic of the transformer circuit board.

Transformer printed circuit card 52 is better understood upon reference to FIG. 10. Electrical receptacle 16 is electrically connected to conventional transformer 60 on printed circuit card 52 and converts 115 V to 24 V. Card 52 also includes conventional double pole double threshold switch 61. Connector 62 is a seven (7) slot connector which receives conventional twenty (20) AWG wires (not shown) to provide the needed connections to card 53 and knob 18.

Figure 11:
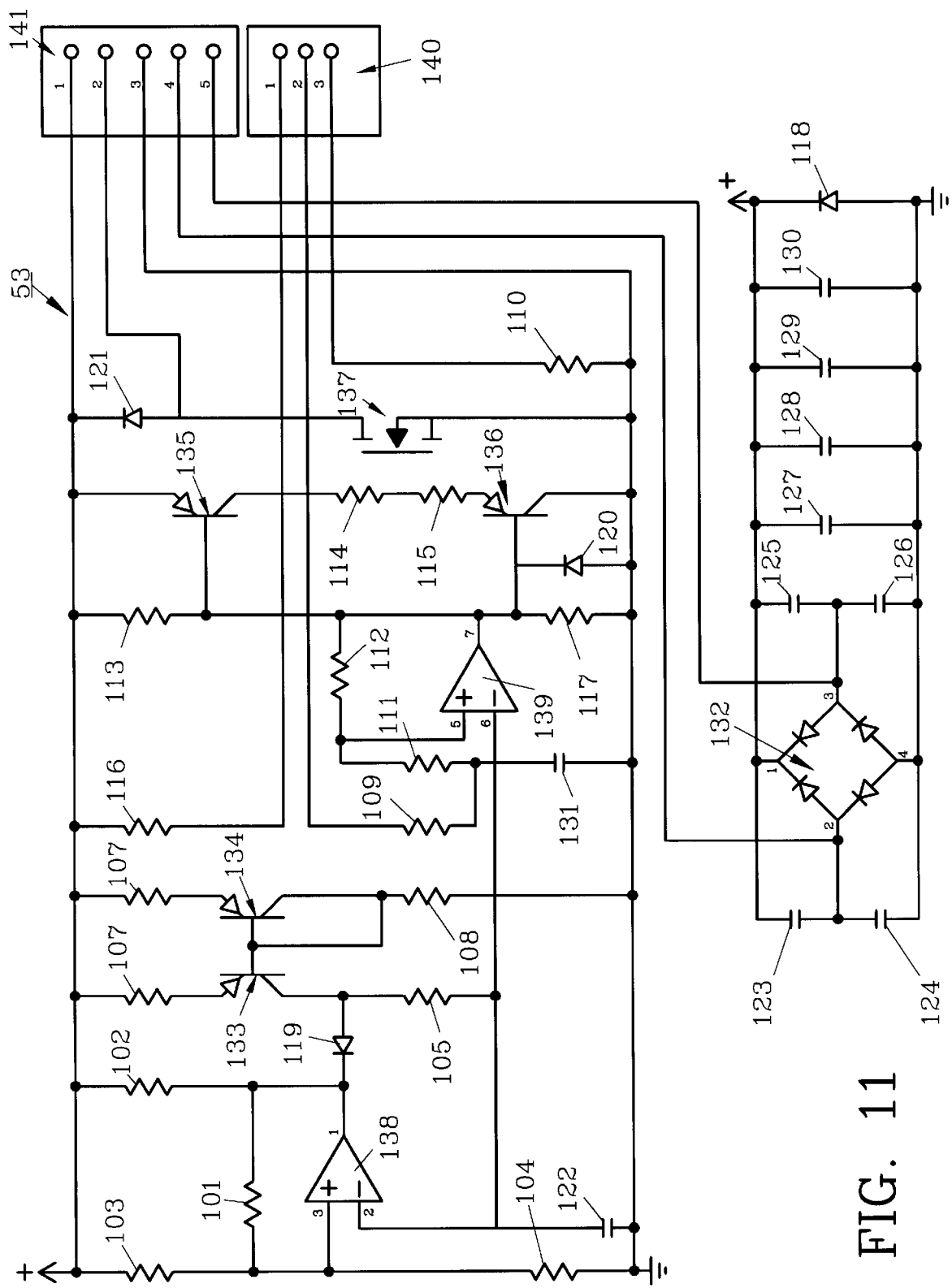
FIG. 11 pictures the electrical schematic for the speed control circuit board.

Card 53 is better understood upon reference to FIG. 11. Card 53 includes resistors 101–117; diodes 118–121; capacitors 122–131; bridge 132; transistors 133–137; amplifiers 138 and 139 and connectors 140 and 141 substantially as shown in FIG. 11.

Resistors 105, 110, 114 and 115 are 100 Ω resistors. Resistors 101, 103 and 104 are 49.9 kΩ resistors. Resistors 102 and 108 are 20 kΩ resistors. Resistors 113 and 117 are 10 kΩ resistors. Resistors 116 is a 8.25 kΩ resistor. Resistor 106 is a 3.32 kΩ resistor. Resistors 107, 109 and 111 are 1 kΩ resistors. Resistor 112 is a 1 MΩ resistor.

Diode 118 is a 1.5 k diode. Diode 119 is a 1N4148 diode. Diode 120 is a 1N5243B diode. Diode 121 is a 1N5822 diode.

Capacitor 122 is a 1000 pF capacitor. Capacitor 127 is a 4700 μF capacitor. Capacitors 123–126 are optional 0.01 μF capacitors which can be used to reduce emissions to comply with FCC emissions standards in the event that bridge 132 emits electromagnetic radiation over the standards. Capacitors 128–131 are 0.1 μF capacitors.

Transistors 133, 134 and 136 are PN2907A transistors. Transistor 135 is a PN222A transistor. Transistor 137 is an IRF540 transistor. Amplifiers 138 and 139 are contained within a LT1018, 8 pin chip. Connector 140 is a conventional 3 pin connector with pins of 0.100 inch or 0.254 cm in diameter. Connector 141 is a convention 5 pin connector with pins of 0.156 inch or 0.396 cm in diameter. Bridge 132 is a conventional 4 diode bridge rated for 4 amps and 400 volts which converts the AC voltage supply to a DC voltage supply as is well understood. Diode 118 acts to prevent transients from bridge 132 from damaging the rest of the circuit.

It should be understood that while specific values and a particular arrangement of elements is described for cards 52 and 53, other equivalent circuits could be constructed as is well understood in the art.

The preceding recitation is provided as an example of the preferred embodiment and is not meant to limit the nature or scope of the present invention or the appended claims.

We claim:

1. A mixing device comprising:
    a) a base, said base comprising a planar member and an x-shaped housing, said x-shaped housing attached to said planar member;
    b) a tiltable platform, said tiltable platform spaced from said base; and
    c) means for selectively adjusting the degree of tilt of said platform relative to said base, said tilt adjusting means connecting said platform to said base.

2. The mixing device of claim 1 further comprising a flexible connector, said flexible connector attaching said base to said platform while providing support thereto.

3. The mixing device of claim 1 further comprising a motor and an arm, said motor rotating said arm, said motor contiguous to said base.

4. The mixing device of claim 3 wherein said tilt adjusting means comprises a collar, said collar threadably joined to said arm, wherein said collar controls the spacing between said base and said platform.

5. The mixing device of claim 4 wherein said tilt adjusting means further comprises a resilient member, said resilient member positioned within said collar to support the same.

6. A mixing device comprising:
    a) a base, said base including a planar member and an x-shaped housing;
    b) a platform, said platform spaced from said base;
    c) a motor, said motor contained within said housing, said motor for rotating said platform;
    d) a flexible connector, said flexible connector attaching said base and said platform, said flexible connector spaced from said housing, said flexible connector creating vertical motion in said platform as said motor rotates the same; and e) means to selectively adjust the degree of tilt of said platform relative to said base.

7. The mixing device of claim 6 further comprising an arm, said arm connected to said motor.

8. The mixing device of claim 6 wherein said flexible connector is formed from a polymeric material.

9. The mixing device of claim 6 further comprising a plurality of flexible connectors, each of said plurality of flexible connectors positioned in the corners of said x-shaped housing.

10. The mixing device of claim 6 wherein said base is made of metal.

11. A method of stirring a solution with a mixing device, said mixing device utilizing a rotatable adjustably tiltable platform spaced from a base, said method comprising the steps of:

a) selectively adjusting the degree of tilt of the platform by compressing a spring positioned within a collar positioned between said platform and said base; and b) rotating the platform to mix the solution.

12. The method of claim 11 further comprising the step of providing power to the mixing device.

13. The method of claim 12 wherein the step of providing power to the mixing device comprises providing electrical power to the mixing device.

14. The method of claim 11 wherein selectively adjusting the degree of tilt of the platform comprises rotating said collar on the mixing device thereby changing the distance between said base and said platform.

15. The method of claim 11 further comprising the step of placing a solution on the platform.

16. A mixing device comprising:

a) a base;

b) a tiltable platform, said tiltable platform spaced from said base; and c) means for selectively adjusting the degree of tilt of said platform relative to said base, said tilt adjusting means connecting said platform to said base, said tilt adjusting means comprises a collar and a resilient member, said collar joined to said platform, said resilient member positioned within said collar to support the same, wherein said collar controls the spacing between said base and said platform.

* * * * *